(12) United States Patent
Simone

(10) Patent No.: US 8,195,323 B2
(45) Date of Patent: Jun. 5, 2012

(54) METHOD AND DEVICE FOR CONTROLLING ADVANCE OF A WEB MATERIAL, CORRESPONDING COMPUTER PROGRAM PRODUCT

(75) Inventor: Giambattista Simone, Spoltore (IT)

(73) Assignee: Fameccanica. Data S.p.A., Sambuceto Di SanGiovanni Teatino (Chieti) (IT)

( * ) Notice: Subject to any disclaimer, the term of this patent is extended or adjusted under 35 U.S.C. 154(b) by 935 days.

(21) Appl. No.: 12/191,126

(22) Filed: Aug. 13, 2008

(65) Prior Publication Data

US 2009/0048702 A1 Feb. 19, 2009

(30) Foreign Application Priority Data

Aug. 14, 2007 (EP) .................................. 07425530

(51) Int. Cl.
*G06F 19/00* (2011.01)
*B44C 1/17* (2006.01)
*B31B 1/00* (2006.01)
*B31B 49/00* (2006.01)
*B31B 1/88* (2006.01)

(52) U.S. Cl. ........ 700/122; 700/123; 700/124; 700/125; 156/64; 156/239; 226/9; 493/3; 493/11; 493/187; 493/382

(58) Field of Classification Search .......... 700/122–125; 156/64, 239; 226/9; 493/3, 11, 187, 382
See application file for complete search history.

(56) References Cited

U.S. PATENT DOCUMENTS 4,528,630 A * 7/1985 Sargent ......................... 700/125

(Continued)

FOREIGN PATENT DOCUMENTS

WO 0045767 A 8/2000

(Continued)

OTHER PUBLICATIONS

European Search Report for Corresponding EP Application No. 07425530.8 dated Feb. 6, 2008.

*Primary Examiner* — Ramesh Patel
(74) *Attorney, Agent, or Firm* — Heslin Rothenberg Farley & Mesiti P.C.; Victor A. Cardona

(57) ABSTRACT

Described herein is a system for controlling advance of a web material having characteristics of extensibility and comprising successive stretches of web for the production of respective articles, such as sanitary articles. In the passage from a delivery assembly to a treatment station functioning cyclically, the web material is subjected to extension. In order to ensure proper alignment of the individual articles with patterns or decorations provided thereon, the web must be fed to the treatment station in phase with the position reached by the treatment station within its operating cycle. A position sensor enables detection, for each stretch of web, of a real position of operation of the treatment station used for feeding the stretch of web itself to the treatment station with the aforesaid given phase relationship. A control module is able to detect the position error between the real position of operation and an ideal position of operation and to control the speed of operation of the delivery assembly to minimize the aforesaid position error. The system is configured for adaptively adjusting the aforesaid reference position so as to compensate for the variations of the characteristics of extensibility of the web material.

15 Claims, 3 Drawing Sheets

U.S. PATENT DOCUMENTS

| | | | |
|---|---|---|---|
| 4,610,739 A * | 9/1986 | Jensen | 156/64 |
| 5,045,135 A * | 9/1991 | Meissner et al. | 156/64 |
| 5,156,793 A * | 10/1992 | Buell et al. | 264/288.8 |
| 5,286,543 A * | 2/1994 | Ungpiyakul et al. | 428/32.24 |
| 5,359,525 A * | 10/1994 | Weyenberg | 700/124 |
| 5,766,389 A | 6/1998 | Brandon et al. | |
| 5,930,139 A * | 7/1999 | Chapdelaine et al. | 700/118 |
| 5,932,039 A * | 8/1999 | Popp et al. | 156/64 |
| 5,964,970 A * | 10/1999 | Woolwine et al. | 156/64 |
| 6,026,172 A * | 2/2000 | Lewis et al. | 382/106 |
| 6,033,502 A * | 3/2000 | Coenen et al. | 156/64 |
| 6,957,160 B2 * | 10/2005 | Miller et al. | 702/94 |
| 2005/0125180 A1 * | 6/2005 | Miller et al. | 702/94 |

FOREIGN PATENT DOCUMENTS

WO          0156525 A          8/2001

* cited by examiner

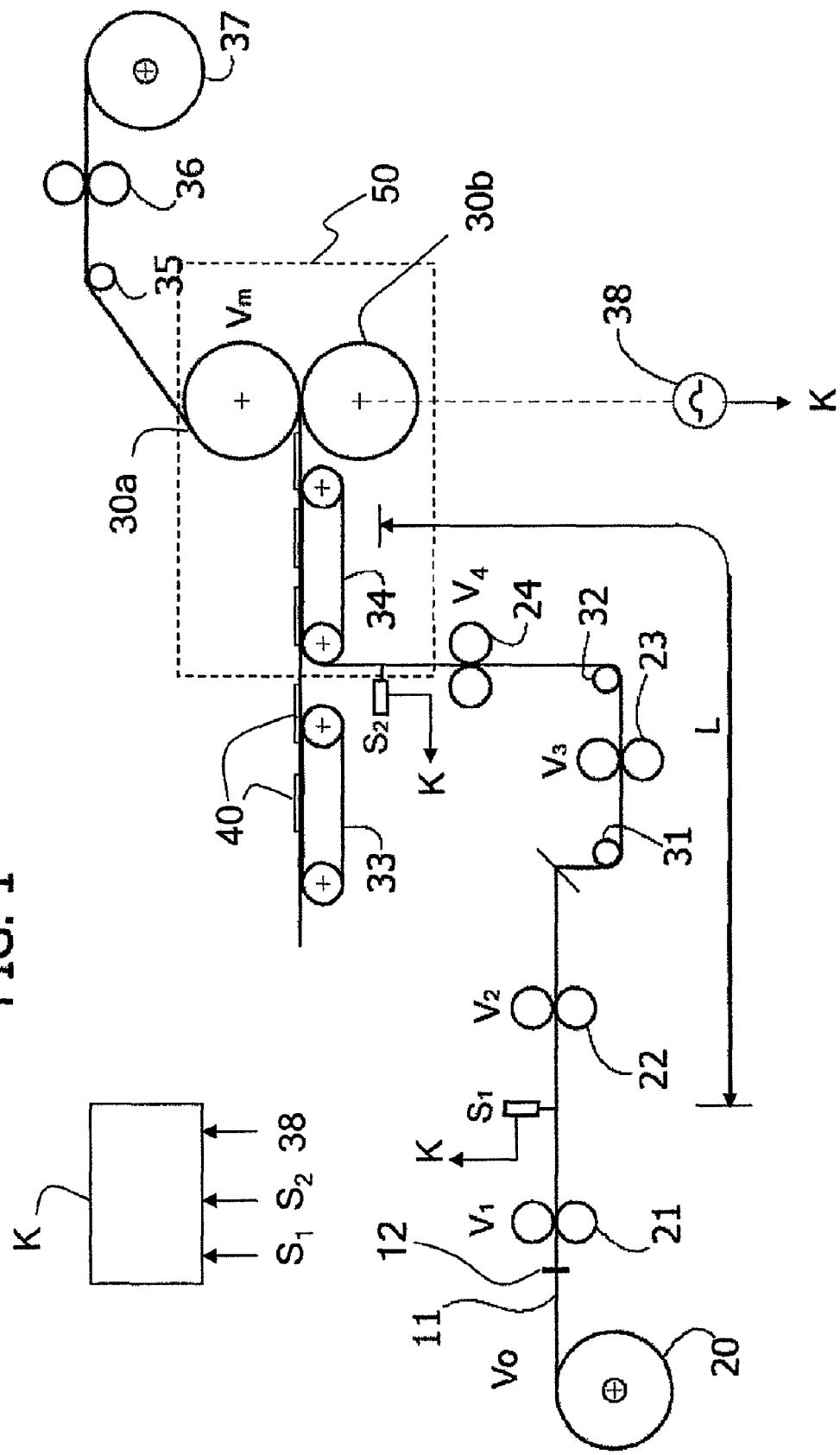

METHOD AND DEVICE FOR CONTROLLING ADVANCE OF A WEB MATERIAL, CORRESPONDING COMPUTER PROGRAM PRODUCT

CROSS-REFERENCE TO RELATED APPLICATIONS

This application claims priority from European patent application Serial No. 07425530.8, filed on Aug. 14, 2007, the entirety of which is hereby incorporated by reference.

FIELD OF THE INVENTION

The invention relates, in general, to techniques for controlling the advance of web materials.

The invention has been developed with particular attention paid to its possible application in processes in which a pre-printed web material (or web) wound off a reel is entrained through movement elements to a processing station, in which further elements are applied on the web.

BACKGROUND ART

A typical context of application in which there arise conditions such as the ones outlined above is the production of disposable absorbent sanitary articles with use of web materials that have characteristics of extensibility.

By "extensibility" (or "elasticity") is meant in general the fact that the material may be subjected to tensile force and extended (lengthened), even to a significant extent, for example 100% of its initial dimension at rest, i.e., with a lengthening of 100%, so that the material is brought to a length equal to twice its length at rest. Very frequently, the materials to be elasticated in sanitary products are materials made up of a number of layers, for example two layers or sheets of non-woven fabric, set and anchored between which is a sheet or web of elastic material.

The extensibility of the web can on the other hand create difficulties during treatment of the material, above all if there is taken into account the fact that the web wound on the reel does not usually present physico-mechanical characteristics (for example the modulus of elasticity or in general the characteristics that determine, given one and the same tensile force or "pull" applied, lengthening and/or "neckdown", with the corresponding values of deformation) that are absolutely constant; said characteristics are in fact subject to a certain degree of variability also within one and the same reel.

In a possible application, the web on the reel is a web of polyethylene (pre)printed on which are patterns and decorations. The printed web is fed through various movement and tensioning elements (such as rollers, nip points, transmission bars or "feathers") until it reaches a treatment or processing station functioning in a cyclic way, which applies on the web further elements such as, for example, absorbent layers, labels, and the like. Said elements are applied on the web at regular intervals apart in space and, from this standpoint, the web can be viewed as being made up of successive stretches, each of which corresponds to a single article that is to be obtained from the web. It is therefore important that the stretches of web should be fed to the processing station in a given phase relationship with respect to the operating cycle of the treatment station. In this way, it is ensured that the elements applied on the web are "in phase" with the patterns and/or decorations present on the web in order to prevent the latter from being "off-centre" or "misaligned" with respect to the individual article produced.

In general, it is possible to control advance of the web to the treatment station in such a way that feeding of the web to the treatment station is constant.

This result can be pursued by applying, for example, a constant-mass-flow model. However, the variability of the characteristics of the web, particularly the variations in elastic modulus, affect said model, so that there arises phase displacement in the conveyance of the web such as to lead to a poor alignment of the pattern at the moment of application of the component.

In order to control the phase of the web, it is in general known to provide reference marks on the web, which have the purpose of enabling identification of the individual stretches of web and detection of said reference marks by means of a purposely provided sensor. For example, the U.S. Pat. No. 5,766,389 describes a method for the production of disposable absorbent articles, which envisages use of a layer bearing components and a layer bearing reference marks. Said layers are designed to be assembled together, and it is envisaged to detect the distance between two successive reference marks in order to control the speed of the layer with reference marks. Similar methods are also known from the U.S. Pat. No. 5,930,139, U.S. Pat. No. 5,932,039, U.S. Pat. No. 5,964,970, and U.S. Pat. No. 6,033,502.

The above solutions do not enable, however, an optimal control of phase displacement that will be able to take into account the variations of the characteristics of extensibility of the treated web material.

SUMMARY OF THE INVENTION

The purpose of the present invention is to provide a solution capable of overcoming the drawbacks intrinsic in the solutions described above, in particular taking into account the phase displacement caused by the variability in the physico-mechanical parameters of the web, advance of which is being controlled.

According to the present invention, said purpose is achieved thanks to a method having the characteristics recalled specifically in the ensuing claims.

The invention also regards a corresponding system, as well as a corresponding computer program product, loadable into the memory of at least one processor and comprising software code portions for performing the steps of the method when the product is run on at least one processor. As used herein, the reference to such a "computer program product" is understood as being equivalent to the reference to a computer-readable means containing instructions for controlling the processing system so as to co-ordinate implementation of the method according to the invention. The reference to "at least one processor" is evidently understood as highlighting the possibility for the present invention to be implemented in a modular and/or distributed form.

The claims form an integral part of the technical teaching provided herein in relation to the invention.

BRIEF DESCRIPTION OF THE DRAWINGS

The invention will now be described, purely by way of non-limiting example, with reference to the annexed drawings, in which:

FIG. 1 is a working diagram of the conveying system operating according to the solution described herein;

DESCRIPTION OF PREFERRED EMBODIMENTS OF THE INVENTION

Figure 3:
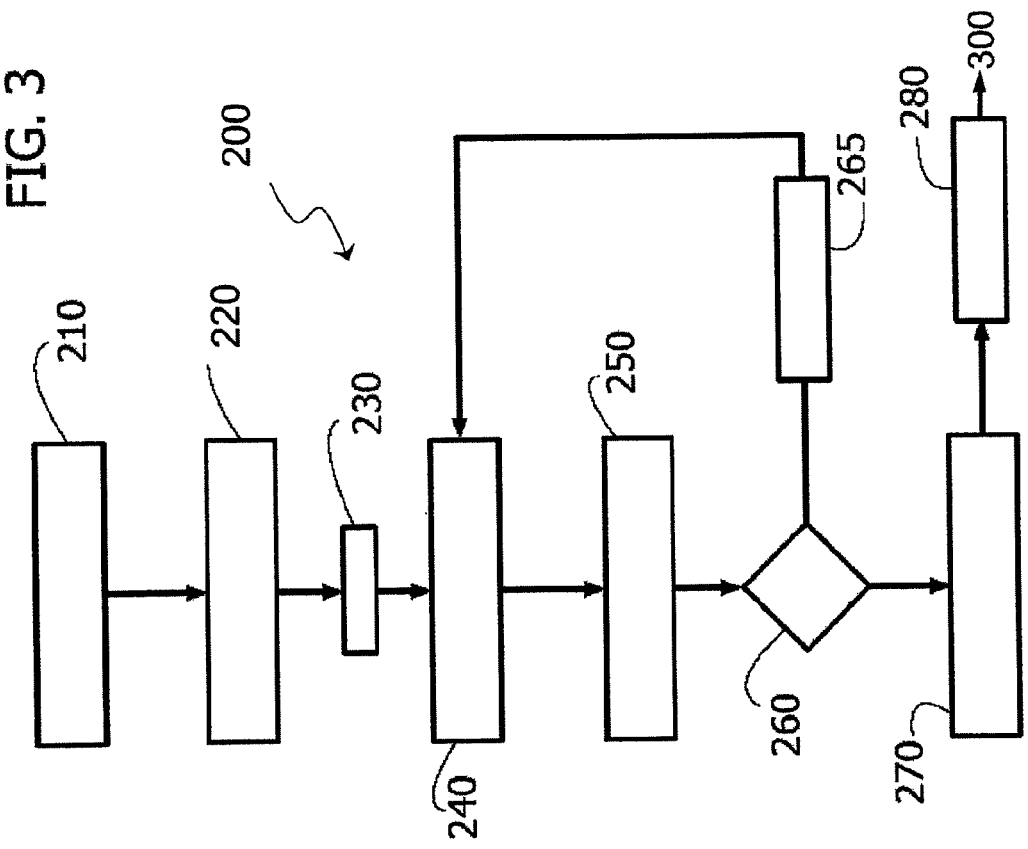
FIGS. 3 and 4 illustrate subsequent portions of a further flowchart illustrating the criteria of operation of the solution described herein

The ensuing detailed description refers, by way of example, to the use of a web of extensible material, which can be used, for example, for the production of disposable sanitary articles.

FIG. 1 represents a schematic working diagram of a system for conveying web according to the solution described herein.

Designated by the reference number 20 is a reel designed to function as source of a web 11, which, in one embodiment, is a web of polyethylene.

The reel 20 impresses a first speed $V_0$ on the web 11. Then, said web 11 is made to pass into a pair of nip points 21 and 22. By "nip point" is meant a set of two rollers, at least one of which is motor-driven, which entrain the web.

The nip points 21 and 22 operate with delivery speeds $V_1$ and $V_2$ that are the same as one another, in such a way as to cause the stretch of web 13 comprised between the nip points 21 and 22 to be regularly distended in such a way as to enable a sensor S1—of a known type—set between the nip points 21 and 22 to detect reference detection marks (notches) 12 set at equal distances apart (only one of which is illustrated, for reasons of simplicity) present on the web 11 and such as to identify successive stretches of the web.

Located downstream of the nip points 21 and 22 are a transmission assembly 31, as well as a subsequent nip point 23 operating at a speed $V_3$, which is followed by a further transmission assembly 32, in turn followed by a further nip point 24 operating at a speed $V_4$.

The nip points 23 and 24 operate at speeds $V_3$ and $V_4$, which are usually the same as one another and are higher than the speeds of the nip points 21 and 22. This has the purpose of subjecting the portion of web 11 set downstream of the nip point 22 to a tensile force that produces longitudinal extension thereof by a desired amount, determined by the difference between the speeds of the nip points in question.

On the other hand, the nip points 23 and 24, with the corresponding transmission assemblies 31 and 32 are to be understood as representing as a whole a set of elements for movement of the web that can be inserted in order to meet the wide range of industrial requirements so as to cause the web to reach a station 50 where an operation of processing/treatment of the web is carried out.

In FIG. 1, the station 50 is represented, by way of example, in the form of a station for application of components 40 such as, for instance, absorbent elements, labels, or the like.

The station 50 comprises a conveyor belt 34, which draws the web 11 towards two application rollers 30a and 30b. A conveyor belt 33 feeds the components 40 (coming from a delivery station of a known type) to the belt 34 so that the components 40 are deposited on the web 11 and conveyed towards the application rollers 30a and 30b, where they are coupled to the web 11.

The application rollers 30a and 30b in turn operate at a speed $V_m$ (which in what follows will be assumed as identical to the speed at which the web 11 exits from the nip point 24), whilst the angle of rotation of said rollers 30a and 30b is measured by an angle detector 38, such as an encoder (which in what follows will be referred to as "master encoder"), which measures "the angle of cycle of the machine", i.e., the position reached at the moment by the treatment station 50 within its operating cycle.

The encoder 38 can be either a real encoder, or a virtual encoder as described, for example, in the article "Single Drive Technology With Electronic Line Shaft Gives New Momentum"—Flexo & Gravure International 2002—p. 66.

In the example of embodiment illustrated, the web 11 bearing the components 40 applied thereon then passes through a transmission element 35 and a nip point 36 and is then finally wound on a second reel 37. In other embodiments, the web 11 with the components 40 can be made to advance to a cutting station, which sees to sectioning it at pre-set distances, thus forming the individual articles starting from the successive stretches of the web 11.

Set downstream of the nip point 24 and upstream of the application station 50 is a second sensor S2 (which is also of a known type, usually the same as the sensor S1), which is also able to detect the reference marks 12 on the web 11.

In this regard, it will be appreciated on the other hand that, whilst the sensor S1 operates on the portion of web 11 comprised between the nip points 21 and 22 (therefore on a web 11 that is certainly distended, but not subjected to a considerable tensile force such as to bring about extension thereof), the sensor S2 operates downstream of the nip point 24, therefore on the extended web that is about to be fed to the station 50.

The conveying system illustrated in FIG. 1 operates under the supervision of a control module K, constituted, for example, by a so-called PLC (Programmable Logic Controller) or by an industrial electronic control system.

Programming of operation of the system on the basis of the indications provided in what follows constitutes a task that falls within the reach of a programmer skilled in the sector and is such as not to require any detailed description herein.

Figure 2:
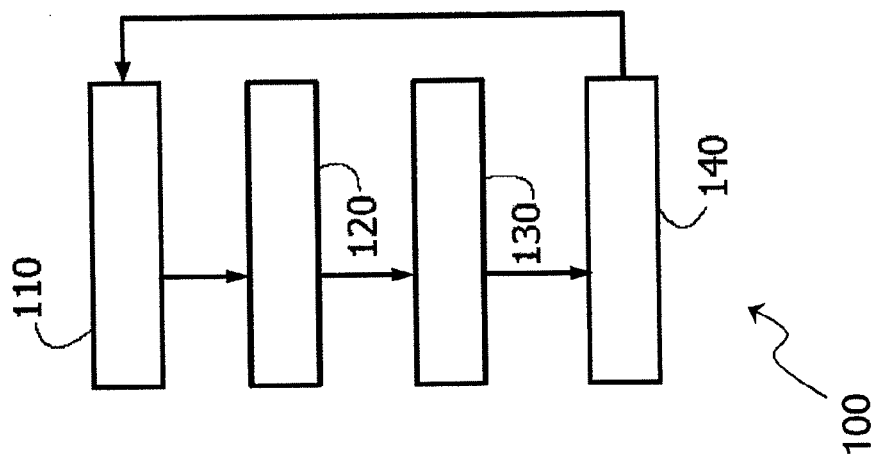
FIG. 2 is a first flowchart illustrating the criteria of operation of the solution described herein.

During the normal cycle of the machine, a correction procedure 100, illustrated also with reference to the flowchart of FIG. 2, envisages the steps described in what follows.

At the moment when, in a step 110, a reference mark 12 is detected by the first sensor S1, a detection signal is sent to the control circuit K, which, in a step 120, acquires via the angle detector 38 the real angular position $\alpha_r$ ("machine angle") of the application roller 30b.

Said real angular position $\alpha_r$ varies in the range 0-360°. For reasons of simplicity of illustration, it will be assumed in what follows that to each stretch of web 11 used for producing a single article there corresponds an entire rotation of the application roller 30b of the station 50.

On the basis of said real angular position $\alpha_r$, read with reference to transit of one of the marks 12 in front of the sensor S1 (in practice, with an action of reading cadenced by the signal of the sensor S1), in a step 130, a first position error $\Delta\alpha$ is calculated as $$\Delta\alpha = \alpha_{id} - \alpha_r \qquad (1)$$

where $\alpha_{id}$ is an ideal angular position, such as to enable correct execution of the operation of application, by properly aligning the pre-printed web 11 and the component 40.

As a function of said first position error $\Delta\alpha$, the control module K corrects, in a step 140, the speed of the nip points 21 and 22 so as to determine a consequent variation of the tension on the stretch of web downstream and, hence, as a result of the variation of the degree of extension of the web that derives therefrom, the consequent variation in the distance of separation between the successive reference marks 12 present on the web fed to the station 50, the purpose being that of minimizing (and virtually cancelling out) the position error $\Delta\alpha = \alpha_{id} - \alpha_r$ between the real angular position $\alpha_r$ and the ideal angular position $\alpha_{id}$, used as reference target of the action of regulation.

In this explanation it is of course assumed that the web 11 traverses the successive nip points 23, 24 without being subjected to further corrections of the movement of advance.

The function of control just described aims at causing the stretch of web 11 designed to define the individual article to arrive in the station 50 in the desired phase relationship referred to the ideal reference position $\alpha_{id}$.

There remains the fact that the corresponding control action envisages:

on the one hand, actions (detection of the marks 12 and control of the speed of advance) made on the web 11 entrained by the nip points 21 and 22, i.e., before said web 11 is subjected to extension, and on the other hand, actions (detection of the machine angle, via the encoder 38) performed where the web is in the extended condition.

The fact that the characteristics of extension of the web 11 vary in time affects said control mechanism causing the latter to end up tracking an ideal reference position $\alpha_{id}$ that not is constant, but varies in time.

Figure 4:
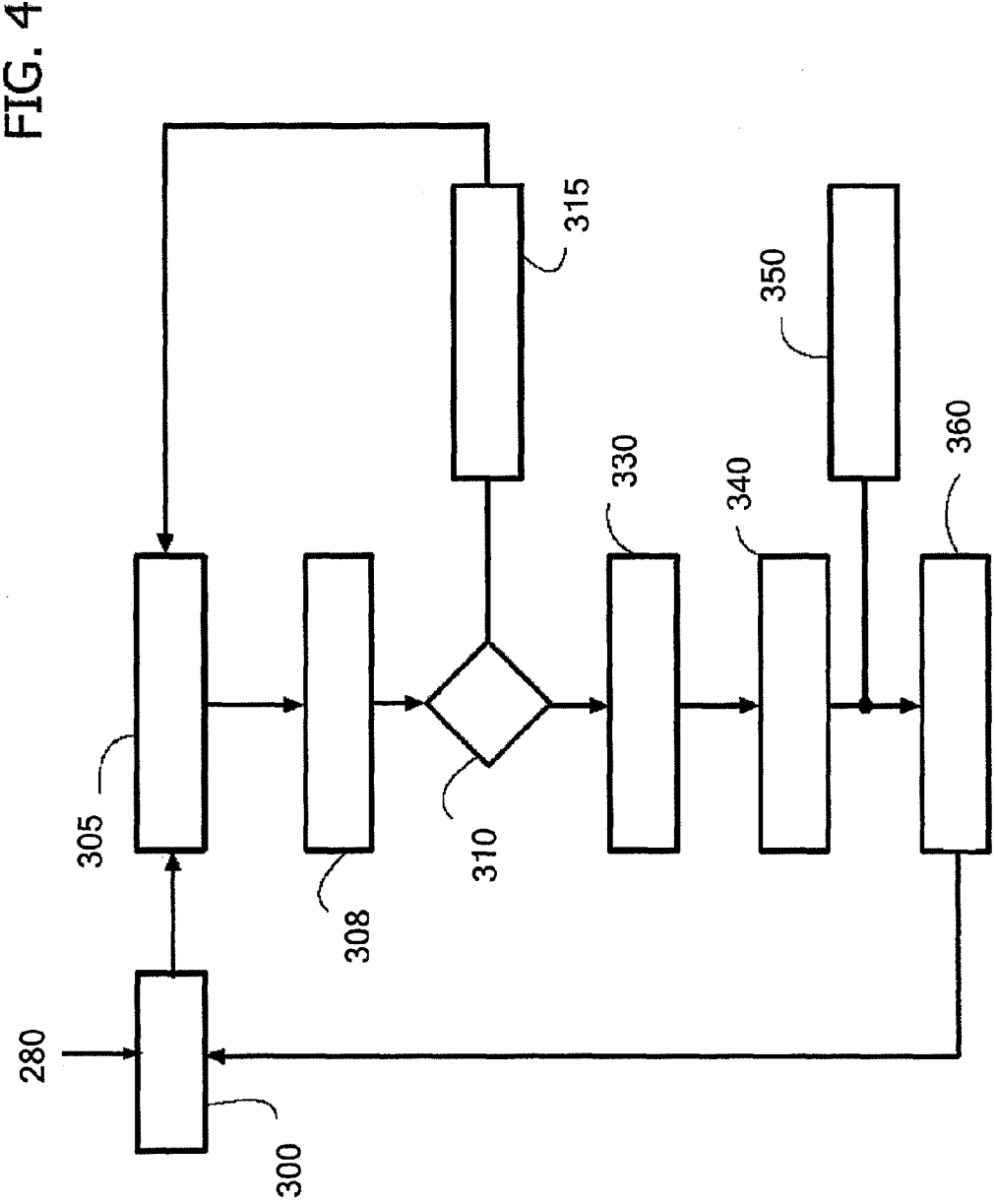

In embodiment referred to specifically in FIGS. 3 and 4 a procedure 200 for "adaptive" regulation of the aforesaid ideal angular position $\alpha_{id}$ is consequently provided.

In the example of embodiment described, said procedure 200 of setting of the ideal angular position is based upon the use of the signal supplied by the second sensor S2. Said procedure is initially carried out following upon a purposely provided command by the machine operator and is then repeated cyclically during operation so as to update the value of the ideal angular position $\alpha_{id}$.

In the embodiment illustrated in FIG. 1, the sensor S2 is located at a distance L with respect to the sensor S1, said distance being understood as length L of the stretch of web 11 comprised between the sensors S1 and S2. Assuming that each article obtained starting from the web 11 corresponds to a stretch of web of length $L_n$, the distance L is determined in such a way that L is equal to approximately n times $L_n$, with n chosen as quite a large integer, for example of the order of some tens; in a possible embodiment n=50.

For reasons of simplicity of illustration, it will be assumed that in the step of start-up of the system, the second sensor S2 is not active. It will be assumed likewise that in a step 210 the control module K detects a value of "experimental" angular position $\alpha_s$, determined by an operator who is seeking the correct setting of the system.

In a subsequent step 220 the second sensor S2 is activated and, from this point, in a step 230 a counter is activated, which initializes a count index m to the value 1.

In a step 240, the sensor S2 detects the first reference mark 12 that transits in front of it and, in a step 250, issues a command for acquisition, via the angle detector 38, of a value of angle $\alpha_i$ of the roller 30b—said angular value indicating the working position (machine angle) at the moment reached by the station 50.

Then, in a testing step 260 a check is made to verify whether the index m is equal to the number n defined previously.

If it is not (i.e., if the index m is other than—in practice is lower than –n), in a step 265 the index m is incremented by 1, and control returns to step 240 where reading of the reference mark 12 by the second sensor S2 occurs.

The blocks 230, 260, 265 hence perform as a whole the function of counting of the number n of articles.

The blocks 230, 260, 265 perform via the encoder 38 iterative acquisition of a number n of corresponding angular positions $\alpha_i$, i.e., of cycle angles of the application station 50.

Said n angular positions $\alpha_i$ are used for calculating in a subsequent calculation step 270 a first value of average angular position $\bar{\alpha}'$ according to the relation:

$$\bar{\alpha}' = \frac{\sum_{i=1}^{n} \alpha_i}{n} \quad (2)$$

The average is made on a number n of products present between the sensor $S_1$ and the sensor $S_2$ so as to detect the effects of the action of control represented by the flowchart of FIG. 2, and possibly to correct said action via variation of the value of $\alpha_{id}$.

In this regard, it will be appreciated that the working position $\alpha_r$ used for the purposes of calculation of the position error $\Delta\alpha$ defined by Eq. (1) given previously is detected with reference to transit of one of the marks 12 in front of the sensor S1, located in the delivery assembly 21, 22 (therefore where the web 11 is not yet extended).

Instead, each working position $\alpha_i$ considered herein for the purposes of calculation of Eq. (2) is detected with reference to transit of one of the marks 12 in front of the sensor S2 (in practice, with an action of reading cadenced by the signal of the sensor S2), hence where the web 11 is in the extended condition, in view of supply to the station 50. Here the different notations ($\alpha_r$ and $\alpha_i$) adopted for designating the working position (machine angle) detected via the sensor 38 according to whether the action of detection is referred to the signal of the sensor S1 or else to the signal of the sensor S2.

In the example of embodiment considered here, the readings made via the sensor S2 have the purpose of verifying the effect produced on the web 1 by the corrections made by the system represented in the flowchart of FIG. 2. In practice, if the system constituted by the two nip points 21 and 22 is tracking a non-correct value of $\alpha_{id}$, the detections made by the sensor $S_2$ will enable within a certain time—as will be described more fully in what follows—correction of the value of $\alpha_{id}$, bringing the system back into the correct working condition.

Thanks to the distance L, the readings referred to the sensor $S_2$ are not affected by possible oscillations produced by the action of correction to which the diagram of FIG. 2 refers, but do on the other hand take into account the average effect of the corrections themselves.

In a step 280, the aforesaid average value is stored as reference value by the control module K.

The sequence of steps just described is then substantially repeated (in a continuous cyclic way or at discrete intervals) during operation of the system.

The flowchart of FIG. 4 relates to the first iteration of the sequence after storage of the reference value.

In particular, in a step 300, the index m is again initialized to the value 1 and in a step 305 the second sensor S2 detects again the passage of a reference mark 12, and then acquires in a step 308 the angular position $\alpha_i$ for each article.

Then, via a testing step 310 a check is again made to verify whether the index m is equal to a number n of products. If it is not, in a step 315 the index m is incremented by 1, and control returns to the step 305 of reading of the reference mark 12 by the sensor S2.

When, from the testing step 310, it is found that there have been acquired n new angular positions $\alpha_i$, in a step 330, in a way similar to step 270, a second angular position $\bar{\alpha}''$ is calculated, which is then compared, in a step 340, with the first average angular position $\overline{\alpha}'$ stored as reference value in order to obtain an average coupling error $\Delta\overline{\alpha}$ according to the relation $$\Delta\overline{\alpha}=\overline{\alpha}'-\overline{\alpha}'' \quad (3)$$

An average coupling error $\Delta\overline{\alpha}$ is thus obtained, which constitutes in practice a measurement of how much the ideal value of the angular position $\alpha_{id}$ is to be varied in order to compensate for the possible change of the characteristics of extensibility of the web 11.

In a step 350 the value of the angular position $\alpha_{id}$ is varied on the basis of the value of the average coupling error $\Delta\overline{\alpha}$ so as to minimize the value of said average coupling error $\Delta\overline{\alpha}$.

In particular, in step 350 it is possible to apply the relation $$\alpha_{id}=\alpha_s+k_p\Delta\overline{\alpha} \quad (4)$$

where the ideal angular position $\alpha_{id}$ used in the correction process 100 that uses the detection of the first sensor S1 is varied proportionally on the basis of a constant $k_p$.

In a step 360, the value of ideal angular position $\alpha_{id}$ is supplied to the correction process 100 so as to control the machine in operation during the cycle.

The constant $k_p$ can be determined in an empirical way so as to optimize the speed of convergence of the feedback system just described.

The same sequence of FIG. 4 is then repeated (see return from step 360 to step 300) during operation, recalculating each time the coupling error $\Delta\overline{\alpha}$ and updating the value $\alpha_{id}$ according to Eq. (4). Of course, since it is an iterative updating method, Eq. (4) is applied according to the expression given above only when the value of the ideal angular position $\alpha_{id}$ has been corrected for the first time. For the subsequent corrections, based upon subsequent sequences of n articles, the value of experimental angular position $\alpha_s$ is replaced by the value of ideal angular position $\alpha_{id}$ calculated in the step 360 of updating referred to above, and the relation applied will hence be $\alpha_{id}=\alpha_{id}+k_p\Delta\overline{\alpha}$.

Of course, without prejudice to the principle of the invention, the details of construction and the embodiments may be varied widely, even to a significant extent, with respect to what is described and illustrated herein, without thereby departing from the scope of the present invention, as defined by the annexed claims.

The invention claimed is:

1. A method for controlling advance of a web material having characteristics of extensibility and comprising successive stretches of the web material for the production of respective articles, in which, in the passage from a delivery assembly to a treatment station functioning cyclically, said web material is subjected to extension and in which the stretches of web material are fed in an extended condition to the treatment station in a given phase relationship with respect to the position of the treatment station in the framework of the operating cycle of the treatment station itself, the method comprising:
    identifying a position of operation of the treatment station to be used as a reference position for said given phase relationship;
    detecting, for each stretch of said web material, reference marks on the web material to obtain a real position of operation of the treatment station used for feeding the stretch of said web material to the treatment station with said given phase relationship;
    detecting a position error between said real position of operation and said reference position;
    controlling operation of said delivery assembly in order to minimize said position error,
    detecting the real position of operation under the control of a signal sent by a first sensor operating on a non-extended portion of said web material to calculate a first value of average angular position of the treatment station;
    performing detection of further real positions of operation of the treatment station under the control of a signal sent by a second sensor operating on an extended portion of the web material to calculate a second value of average angular position of the treatment station;
    comparing the value of the first average angular position to the value of the second average angular position to obtain a coupling error; and
    adjusting said reference position adaptively on the basis of the coupling error, so as to compensate for the variations of the characteristics of extensibility of said web material.

2. The method according to claim 1, in which said operation of adaptively adjusting said reference position comprises:
    detecting, for a first plurality of successive stretches of said web material, a first average value of the real positions of operation of the treatment station used for feeding the stretches of said web material of said first plurality to the treatment station with said given phase relationship;
    detecting, for at least one further plurality of successive stretches of said web material, at least one further average value of the real positions of operation of the treatment station used for feeding the stretches of web of said at least one further plurality to the treatment station with said given phase relationship;
    detecting a deviation between said first average value and said at least one further average value, said deviation indicating an error of coupling of said web material with said treatment station; and
    adaptively adjusting said reference position as a function of said coupling error.

3. The method according to claim 2, comprising repeating said operations of detection of at least one further average value, detecting said deviation indicating said coupling error and adaptively adjusting said reference position as a function of said coupling error for a set of a further plurality of successive stretches of said web material during advance of the web material.

4. The method according to claim 2, wherein said operation of adaptive adjustment comprises adapting said reference position proportionally to said coupling error.

5. The method according to claim 1, wherein said operation of detection of said first average value and said at least one further average value of the real positions of operation of the treatment station for the purposes of detecting said error of coupling of said web material with said treatment station is referred to the transit of stretches of said web material fed in the extended condition to the treatment station itself.

6. The method according to claim 1, wherein said operation of detection of the real position of operation of the treatment station for the purposes of detecting said position error is referred to the transit of one stretch of said web material delivered by said delivery assembly.

7. A computer program product, which loadable into the memory of at least one processor and comprising software code portions for performing the method according to claim 1.

8. A system for controlling advance of a web material having characteristics of extensibility and comprising successive stretches of said web material for the production of respective articles, in which, in the passage from a delivery assembly to a treatment station functioning cyclically, said web material is subjected to extension and in which the stretches of web material are fed in an extended condition to the treatment station in a given phase relationship with respect to the position of the treatment station in the framework of the operating cycle of the treatment station itself, the system comprising:

a position sensor, which can detect, for each stretch of said web material, a real position of operation of the treatment station used for feeding the stretch of web itself to the treatment station with said given phase relationship;

a control module, which communicates with said position sensor and is configured to detect a position error between said real position of operation and a reference position of operation of the treatment station to be used as reference for said given phase relationship, said control module being configured for controlling operation of said delivery assembly in order to minimize said position error;

a first further sensor, which is sensitive to the transit of reference marks identifying said successive stretches of said web material when said web material is in a non-extended condition as delivered by said delivery assembly;

a second further sensor, which is sensitive to the transit of said reference marks identifying said successive stretches of said web material fed in the extended condition to said treatment station;

said control module being configured for detecting the real position of operation of the treatment station:
  a) in transit, detected by said first further sensor, of a reference mark identifying a stretch of said web material delivered by said delivery assembly for the purposes of detecting said position error; and
  b) in transit, detected by said second further sensor, of reference marks identifying stretches of said web material fed in the extended condition to the treatment station itself for the purposes of detecting a first average value of average angular position of the treatment station and said at least one further average value of average angular position of the treatment station and detecting said error of coupling of said web material with said treatment station; and said system configured for adaptively adjusting said reference position on the basis of the coupling error so as to compensate for the variations of the characteristics of extensibility of said web material.

9. The system according to claim 8, wherein in order to carry out said operation of adaptively adjusting said reference position, the system is configured for:

detecting, for a first plurality of successive stretches of said web material, a first average value of the real positions of operation of the treatment station used for feeding the stretches of said web material of said first plurality to the treatment station with said given phase relationship;

detecting, for at least one further plurality of successive stretches of said web material, at least one further average value of the real positions of operation of the treatment station used for feeding the stretches of said web material of said at least one further plurality to the treatment station with said given phase relationship;

detecting the deviation between said first average value and said at least one further average value, said deviation indicating an error of coupling of said web material with said treatment station; and adaptively adjusting said reference position as a function of said coupling error.

10. The system according to claim 9, the system being configured for repeating said operations of detection of at least one further average value, detecting said deviation indicating said coupling error and adaptively adjusting said reference position as a function of said coupling error for a set of further pluralities of successive stretches of said web material during advance of the web material.

11. The system according to claim 9, wherein to carry out said operation of adaptively adjusting, the system is configured for adapting said reference position proportionally to said coupling error.

12. The system according to claim 8, wherein said first further sensor and said second further sensor are separated by a distance, referred to said web material, corresponding to a multiple of the length of said stretches of web material.

13. The system according to claim 12, configured for detecting said first average value and said at least one further average value on a first plurality and at least one further plurality of successive stretches of said web material comprising stretches of web in a number equal to said multiple.

14. The system according to claim 12, wherein said multiple is of the order of tens.

15. The system of claim 14, wherein said multiple comprises about 50.

* * * * *

UNITED STATES PATENT AND TRADEMARK OFFICE
CERTIFICATE OF CORRECTION

PATENT NO.       : 8,195,323 B2
APPLICATION NO.  : 12/191126
DATED            : June 5, 2012
INVENTOR(S)      : Giambattista Simone It is certified that error appears in the above-identified patent and that said Letters Patent is hereby corrected as shown below:

Column 8, Line 60: Claim 7, Delete "computer program product" and insert
-- non-transitory computer program product --

Signed and Sealed this
Seventh Day of August, 2012

David J. Kappos
*Director of the United States Patent and Trademark Office*